US00PP24540P2

(12) United States Plant Patent
Tas

(10) Patent No.: US PP24,540 P2
(45) Date of Patent: Jun. 10, 2014

(54) ***ALSTROEMERIA* PLANT NAMED 'TESRONTO IMP'**

(50) Latin Name: *Alstroemeria hybrida*
Varietal Denomination: Tesronto Imp

(75) Inventor: Marius Tas, De Kwakel (NL)

(73) Assignee: VOF Hortipartners, Heerhugowaard (NL)

( * ) Notice: Subject to any disclaimer, the term of this patent is extended or adjusted under 35 U.S.C. 154(b) by 166 days.

(21) Appl. No.: 13/506,697

(22) Filed: May 10, 2012

(51) Int. Cl.
*A01H 5/00* (2006.01)

(52) U.S. Cl.
USPC ..... Plt./309

(58) Field of Classification Search
USPC ..... Plt./309
See application file for complete search history.

*Primary Examiner* — June Hwu
(74) *Attorney, Agent, or Firm* — C. A. Whealy

(57) ABSTRACT

A new and distinct cultivar of *Alstroemeria* plant named 'Tesronto Imp', characterized by its tall, upright and somewhat outwardly spreading plant habit; sturdy and strong plants; moderately vigorous growth habit; large and numerous red, orange and yellow-colored flowers; and good garden performance.

1 Drawing Sheet

Botanical designation: *Alstroemeria hybrida.*
Cultivar denomination: 'TESRONTO IMP'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tesronto Imp'.

The new *Alstroemeria* plant is a product of a planned breeding program conducted by the Inventor in Heerhugowaard, The Netherlands. The objective of the breeding program is to create new potted garden *Alstroemeria* plants that flower continuously and with numerous attractive flowers.

The new *Alstroemeria* plant is a naturally-occurring branch mutation of *Alstroemeria hybrida* 'Tesronto', not patented. The new *Alstroemeria* plant was discovered and selected by the Inventor on a single flowering plant from within a population of plants of 'Tesronto' in a controlled greenhouse environment in Heerhugowaard, The Netherlands in June, 2008.

Asexual reproduction of the new *Alstroemeria* plant by root divisions in a controlled greenhouse environment in Heerhugowaard, The Netherlands since September, 2008 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tesronto Imp'. These characteristics in combination distinguish 'Tesronto Imp' as a new and distinct *Alstroemeria* plant:

1. Tall, upright and somewhat outwardly spreading plant habit.
2. Sturdy and strong plants; moderately vigorous growth habit.
3. Large and numerous red, orange and yellow-colored flowers.
4. Good garden performance.

Plants of the new *Alstroemeria* can be compared to plants of the mutation parent, 'Tesronto'. Plants of the new *Alstroemeria* differ from plants of 'Tesronto' in the following characteristics:

1. Plants of the new *Alstroemeria* are larger and more vigorous than plants of 'Tesronto'.
2. Plants of the new *Alstroemeria* have larger flowers than plants of 'Tesronto'.

Plants of the new *Alstroemeria* can be compared to plants of the *Alstroemeria hybrida* 'Tesluco', not patented. In side-by-side comparisons, plants of the new *Alstroemeria* differ primarily from plants of 'Tesluco' in the following characteristics:

1. Plants of the new *Alstroemeria* are shorter than plants of 'Tesluco'.
2. Plants of the new *Alstroemeria* have smaller leaves than plants of 'Tesluco'.
3. Plants of the new *Alstroemeria* have smaller flowers than plants of 'Tesluco'.
4. Plants of the new *Alstroemeria* and 'Tesluco' differ in flower color as plants of 'Tesluco' have orange and yellow-colored flowers.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant.

The photograph comprises a side perspective view of a typical flowering plant of 'Tesronto Imp' grown in a container.

DETAILED BOTANICAL DESCRIPTION

The aforementioned photograph and following observations and measurements describe plants of the new *Alstroemeria* grown during the autumn in 25-cm containers in a glass-covered greenhouse in De Kwakel, The Netherlands. During the production of the plants, day temperatures ranged from 16° C. to 22° C. and night temperatures ranged from 15° C. to 17° C. Plants were 20 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Tesronto Imp'.

Parentage: Naturally-occurring branch mutation of *Alstroemeria hybrida* 'Tesronto', not patented.

Propagation:

*Type.*—By root divisions.

*Time to produce a rooted young plant, summer.*—About seven weeks at 20° C.

*Time to produce a rooted young plant, winter.*—About eight weeks at 16° C.

*Root description.*—Fibrous and fleshy; white in color.

*Rooting habit.*—Freely branching; medium density.

*Rhizome length.*—About 3 cm.

*Rhizome diameter.*—About 5 mm.

*Rhizome texture.*—Smooth.

*Rhizome color.*—Close to 195B.

Plant description:

*Plant and growth habit.*—Herbaceous perennial; tall, upright and somewhat outwardly spreading plant habit, inverted triangle; freely branching habit with about 25 primary lateral branches developing per plant; sturdy and strong plants; moderately vigorous growth habit.

*Plant height.*—About 76 cm.

*Plant diameter* (*area of spread*).—About 72 cm.

Lateral branch description:

*Aspect.*—Mostly upright to somewhat outwardly spreading.

*Length.*—About 48.8 cm.

*Diameter.*—About 5 mm.

*Internode length.*—About 1.8 cm.

*Strength.*—Moderately strong.

*Texture.*—Smooth, glabrous.

*Color.*—Close to 200C finely dotted with close to 144A to 144C.

Foliage description:

*Arrangement.*—Alternate; below the peduncles in a single whorl; simple.

*Length.*—About 8.2 cm.

*Width.*—About 2.9 cm.

*Shape.*—Ovate to elliptic; twisting.

*Apex.*—Acute.

*Base.*—Cuneate.

*Margin.*—Entire.

*Texture, upper and lower surfaces.*—Smooth, glabrous.

*Venation pattern.*—Parallel.

*Color.*—Developing leaves, upper surface: Close to 143A; surface facing upwards, strongly tinged with close to 199A. Developing leaves, lower surface: Close to 143A; surface facing upwards, strongly tinged with close to 200C to 200D. Fully expanded leaves, upper surface: Close to 147A; venation, close to 146A. Fully expanded leaves, lower surface: Close to 147A; surface facing downwards, close to N137A; venation, close to 147B.

*Petioles.*—Length: About 3.3 cm. Diameter: About 1 mm to 7 mm. Color: Close to 148A.

Flower description:

*Flower type and habit.*—Single zygomorphic flowers arranged in compound umbels; flowers face mostly outwardly to slightly upright; perianth segments separate; freely flowering habit with about 13 flowers developing per inflorescence and about 325 flowers developing per plant.

*Natural flowering season.*—Plants begin flowering about eight weeks after planting; flowering continuous from summer into the autumn in The Netherlands.

*Fragrance.*—None detected.

*Flower longevity on the plant.*—About ten days; flowers not persistent.

*Flower buds.*—Length: About 3.3 cm. Diameter: About 1.2 cm. Shape: Narrowly obovate. Color: Close to 185A.

*Umbel height.*—About 11.5 cm.

*Umbel diameter.*—About 16.5 cm.

*Flower diameter* (*horizontal*).—About 5 cm.

*Flower length* (*vertical*).—About 6.3 cm.

*Flower depth* (*height*).—About 5.7 cm.

*Perianth.*—Arrangement: Six arranged in two whorls, each whorl with two lateral and one median segments. Size, inner perianth: Length, lateral segments: About 5.5 cm. Width, lateral segments: About 2 cm. Length, median segment: About 5.1 cm. Width, median segment: About 1.8 cm. Size, outer perianth: Length, lateral segments: About 5.6 cm. Width, lateral segments: About 2.9 cm. Length, median segment: About 5.4 cm. Width, median segment: About 2.8 cm. Shape, inner perianth, lateral and median segments: Oblanceolate. Shape, outer perianth, lateral and median segments: Obovate. Apex, inner perianth, lateral and median segments: Abruptly acute. Apex, outer perianth, lateral and median segments: Emarginate. Base, inner perianth, lateral and median segments: Narrowly cuneate. Base, outer perianth, lateral and median segments: Long cuneate. Margin, inner perianth, lateral and median segments: Entire. Margin, outer perianth, lateral and median segments: Towards the apex, finely serrate; towards the base, entire. Texture, inner and outer perianths, lateral and median segments: Smooth, glabrous; slightly velvety. Color, inner perianth: When opening, lateral segments, upper surface: Close to 3B; towards the apex, close to 46A; spots, close to 203A to 203B. When opening, median segment, upper surface: Close to 3C; towards the apex, close to 46A; spots, close to 203A. When opening, lateral segments, lower surface: Close to 3B; towards the apex, close to 53B to 53C; spots, close to N200B. When opening, median segment, lower surface: Close to 4C; towards the apex, close to 53B to 53C; spots, close to N200B. Fully opened, lateral segments, upper surface: Close to 7A; towards the apex, close to 46A; spots, close to 203A to 203B. With development, color becoming closer to 13C; towards the apex, close to 46A; towards the base, close to 47C; spots, close to 200D. Fully opened, median segment, upper surface: Close to 6C; towards the apex, close to 46A to 46B; spots, close to 203A. With development, color becoming closer to 13C; towards the apex, close to 46A; towards the base, close to 47C; spots, close to 200D. Fully opened, lateral segments, lower surface: Close to 6A; towards the apex, close to 42B; base tinged with close to 42C; spots, close to 203A to 203B. Fully opened, median segment, lower surface: Close to 8B; towards the apex, close to between 42B and 43A; base tinged with close to 41D; spots, close to 203A. Color, outer perianth: When opening, lateral segments, upper surface: Towards the base, close to 161D; towards the apex, Close to 45C; apex, close to 53A; margins, close to 16D. When opening, median segment, upper surface: Towards the base, close to 160C to 160D; towards the apex, close to 45C; apex, close to 53A; margins, close to 16C. When opening, lateral and median segments, lower surface: Close to N34A; towards the apex, close to 53A to almost 203A; margins, close to 16D. Fully opened, lateral and median segments, upper surface: Close to between 45B and 53B; towards the apex, close to 53A to almost 203A; base, close to 160D; margins, close to 29A. With development, color becoming closer to 179D; distal blotch, close to 53D; towards the apex, close to 53A to almost 203A; margins, close to 37C. Fully opened, lateral and median segments, lower surface: Close to 45B; towards the apex, close to 203A; base, close to 45C; margins, close to between 18B to 19B.

*Pedicels.*—Length: About 2.3 cm. Diameter: About 2.5 mm. Strength: Moderately strong. Angle: About 15° from vertical. Texture: Smooth, glabrous. Color, upper surface: Close to 186C. Color, lower surface: Close to 146B.

*Reproductive organs.*—Stamens: Quantity per flower: Six. Filament length: About 4.3 cm. Filament color: Close to 46A; towards the base, close to 150D. Anther shape: Three are oblong and the other three are reniform. Anther length, oblong anthers: About 8 mm. Anther length, reniform anthers: About 3 mm. Anther color: Close to 152B to 152C. Pollen amount: Moderate. Pollen color: Close to 153D. Pistils: Quantity per flower: One. Pistil length: About 4.4 cm. Style length: About 3.9 cm. Style color: Close to 50A; towards the base, lighter than 50A. Stigma shape: Tri-parted; parts, club-shaped, curved. Stigma color: Close to 48B to 48D. Ovary color: Close to 143C tinged with between 197A and N200B.

*Fruits and seeds.*—Fruit and seed development have not been observed on plants of the new *Alstroemeria*.

Disease & pest resistance: Plants of the new *Alstroemeria* have not been observed to be resistant to pathogens and pests common to *Alstroemeria* plants.

Garden performance: Plants of the new *Alstroemeria* have been observed to have good garden performance and to tolerate wind and rain. Plants of the new *Alstroemeria* have been observed to tolerate high temperatures of about 35° C. and to be hardy to USDA Hardiness Zone 8.

It is claimed:

1. A new and distinct *Alstroemeria* plant named 'Tesronto Imp' as illustrated and described.

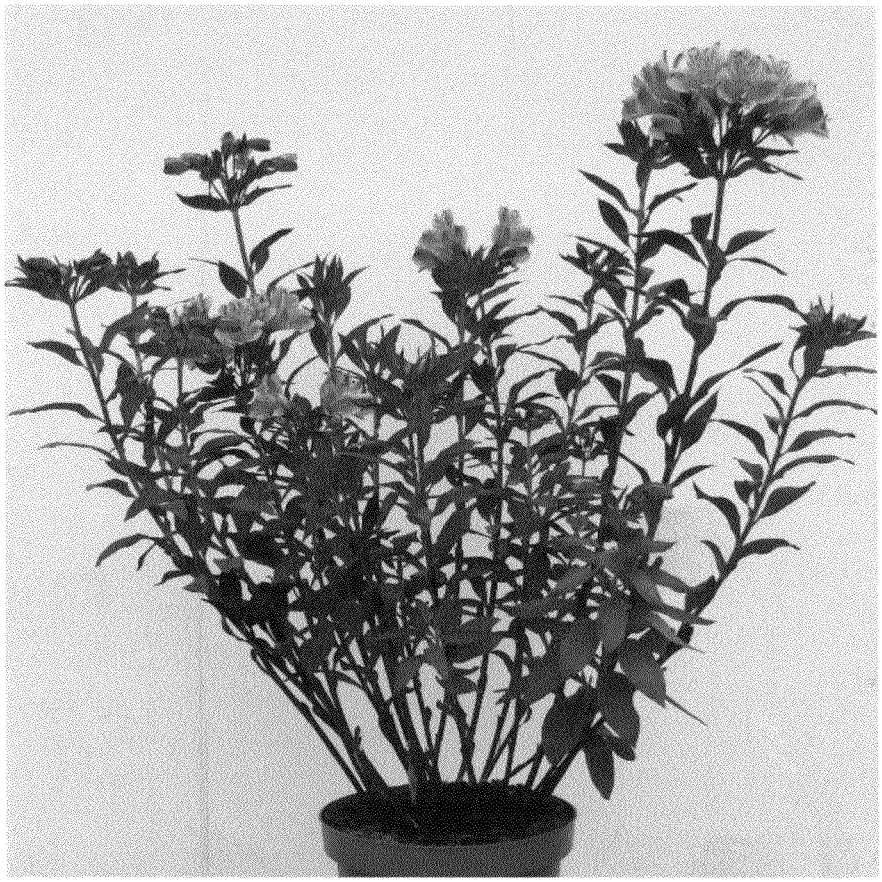

* * * * *